(12) United States Patent
Karam

(10) Patent No.: US 10,884,140 B2
(45) Date of Patent: *Jan. 5, 2021

(54) RADIATION SURVEY PROCESS

(71) Applicant: All Clear Technologies, LLC, Corpus Christi, TX (US)

(72) Inventor: Philip Andrew Karam, Brooklyn, NY (US)

(73) Assignee: All Clear Technologies, LLC, Corpus Christi, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/354,493

(22) Filed: Mar. 15, 2019

(65) Prior Publication Data

US 2020/0081138 A1 Mar. 12, 2020

Related U.S. Application Data

(63) Continuation of application No. 15/917,189, filed on Mar. 9, 2018, now Pat. No. 10,254,416, which is a continuation-in-part of application No. 14/671,783, filed on Mar. 27, 2015, now Pat. No. 9,958,553.

(60) Provisional application No. 62/072,424, filed on Oct. 30, 2014, provisional application No. 62/065,239, filed on Oct. 17, 2014.

(51) Int. Cl.
| | |
|---|---|
| *G01T 1/18* | (2006.01) |
| *G01T 1/167* | (2006.01) |
| *G01N 5/02* | (2006.01) |
| *G01T 1/00* | (2006.01) |
| *G01N 33/24* | (2006.01) |

(52) U.S. Cl.
CPC ............. *G01T 1/18* (2013.01); *G01N 5/025* (2013.01); *G01T 1/00* (2013.01); *G01T 1/167* (2013.01); *G01N 33/24* (2013.01)

(58) Field of Classification Search
None
See application file for complete search history.

(56) References Cited

U.S. PATENT DOCUMENTS

| | | | |
|---|---|---|---|
| 9,958,553 B2 | 4/2018 | Karam | |
| 10,254,416 B2 * | 4/2019 | Karam | ............ G01T 1/18 |
| 2014/0264049 A1 | 9/2014 | Yocum et al. | |

OTHER PUBLICATIONS

International Search Report and Written Opinion for Application No. PCT/US2019/021176 dated Apr. 8, 2019.

* cited by examiner

*Primary Examiner* — David P Porta
*Assistant Examiner* — Mamadou Faye
(74) *Attorney, Agent, or Firm* — Tumey L.L.P.

(57) ABSTRACT

A method for determining a radionuclide concentration of a material is provided. The method comprises placing a detector in a protective structure, wherein the detector is coupled to a single-channel analyzer. The method further comprises inserting the protective structure in a material, wherein the material comprises a radionuclide. The method additionally comprises measuring the moisture content of the material to be analyzed. The method also comprises counting the emitted radiation having a known energy over an interval of time to produce a count per time, wherein the emitted radiation is emitted from the radionuclide and then dividing the count per time by the weight of the material to produce a count per time per weight.

20 Claims, 2 Drawing Sheets

RADIATION SURVEY PROCESS

CROSS-REFERENCE TO RELATED APPLICATIONS

This application is a continuation of U.S. patent application Ser. No. 15/917,189 filed Mar. 9, 2018 which is a continuation-in-part that claims priority to U.S. application Ser. No. 14/671,783 filed on Mar. 27, 2015, which claims priority to U.S. Application Ser. No. 62/065,239 filed on Oct. 17, 2014, and to U.S. Application Ser. No. 62/072,424 filed on Oct. 30, 2014, the disclosures of which are herein incorporated by reference in their entirety.

BACKGROUND OF THE INVENTION

Field of the Invention

This invention relates to the field of radionuclide detection and characterization; and more specifically to the quantification of radionuclides by measurement of single-energy gamma rays in a fixed-geometry system.

Background of the Invention

A number of industries, including oil and gas production, rare earth mineral processing, and phosphate rock processing, generate waste contaminated with radioactive materials. These radioactive materials are generally referred to as naturally occurring radioactive materials (NORM) or technologically enhanced naturally occurring radioactive materials (TENORM). NORM and TENORM are not man-made radioactive materials and are not produced by splitting atoms in a nuclear reactor or by bombarding atoms with subatomic particles in accelerators. In the case of TENORM, the radionuclides may be enhanced by man, for example, by concentration of the radionuclides, but like NORM, TENORM is not produced by man. Some of the radioactive materials in NORM and TENORM may be subject to environmental regulations and require special disposal. NORM and TENORM may include radionuclides such as U-238, U-235, Th-232 as well as their respective progeny radionuclides (e.g., Ra-226, Po-210, etc.). As U-238, U-235, Th-232 and the unstable isotopes of their progeny decay; alpha, beta, and gamma radiation may be emitted. Radiation may continue to be emitted until a stable isotope in the chain of decaying progeny is reached, for example, Pb-206 is a stable isotope and the end product of the U-238 decay chain. The emitted radiation from the unstable radionuclides may be detected and used to calculate the concentration and activity of the unstable radionuclides, and more particularly, those unstable radionuclides which are subject to environmental regulation.

Present techniques for the detection of NORM and TENORM involve extracting samples from a suspect material (e.g., a waste) and then sending each individual sample to a laboratory for analysis, or performing gamma spectroscopy in the field. Laboratory analysis may be costly in both time and expense. For example, a typical laboratory analysis of a sample may take weeks and require expensive and rigorous sample processing. Further, during the time in which a sample is being analyzed, the remainder of the suspect material may be moved to and stored in a holding facility until the laboratory has completed the sample analysis. Also, as discussed above, each and every sample may be sent to the laboratory for analysis. Thus, any time a new waste material is produced or a NORM/TENORM survey is needed for any other reason, samples may be extracted and sent to the laboratory for analysis.

Alternatively, field analysis may be done using specialized equipment. For example, the activity of radionuclides may be measured using a multi-channel analyzer that scans a wide range of gamma ray energies, allowing for the identification and quantification of photons with energies corresponding to the applicable radionuclide progeny. This, multi-channel analysis for gamma radiation (gamma spectroscopy) may require careful sample preparation, and may include drying the sample, weighing a measured amount for analysis, and counting using a gamma spectroscopy system for a time ranging from several minutes to many hours. This technique is complex and may require an involved sample preparation procedure. Further, multi-channel analyzers used to capture multiple emitted gamma rays at once are expensive. Lastly, the operation of multi-channel analyzers is complex and may require trained personnel to operate in order to produce accurate measurements, for example, some radionuclides may emit radiation of an energy which obscures or may be confused with the emitted radiation of another radionuclide desired for analysis. Without proper training, it may be difficult to distinguish between the two activities of the radionuclides and thusly, an inaccurate measurement may be produced.

Consequently, there is a need for an improved radiation survey process for a practical cost-effective method of quantifying the amount of radionuclides in a waste sample in the field.

BRIEF SUMMARY OF SOME OF THE PREFERRED EMBODIMENTS

These and other needs in the art are addressed in an embodiment comprising a method for determining a radionuclide concentration of a material. The method comprises placing the material to be analyzed into a vessel, wherein the material may be contaminated with one or more radionuclides, wherein the material has a known volume, and wherein the vessel has a fixed geometry. The method further comprises weighing the material to be analyzed and measuring the moisture content of the material to be analyzed. The method additionally comprises placing a protective structure in the material and placing a detector in the protective structure, wherein the detector is coupled to a single-channel analyzer. The method also comprises counting the emitted radiation having a known energy over an interval of time to produce a count per time, wherein the emitted radiation is emitted from the radionuclide and then dividing the count per time by the weight of the material to produce a count per time per weight.

These and other needs in the art are addressed by an additional embodiment comprising a system for characterizing the radionuclide content of a material. The system comprises a vessel having a fixed geometry, wherein the vessel is capable of containing a material that may be contaminated with one or more radionuclides. The system further comprises a protective structure inserted into the vessel and a detector inserted into the protective structure, wherein the detector is coupled to a single-channel analyzer.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

These drawings illustrate certain aspects of some of the embodiments of the present method, and should not be used to limit or define the method.

DETAILED DESCRIPTION OF THE PREFERRED EMBODIMENTS

Figure 1:
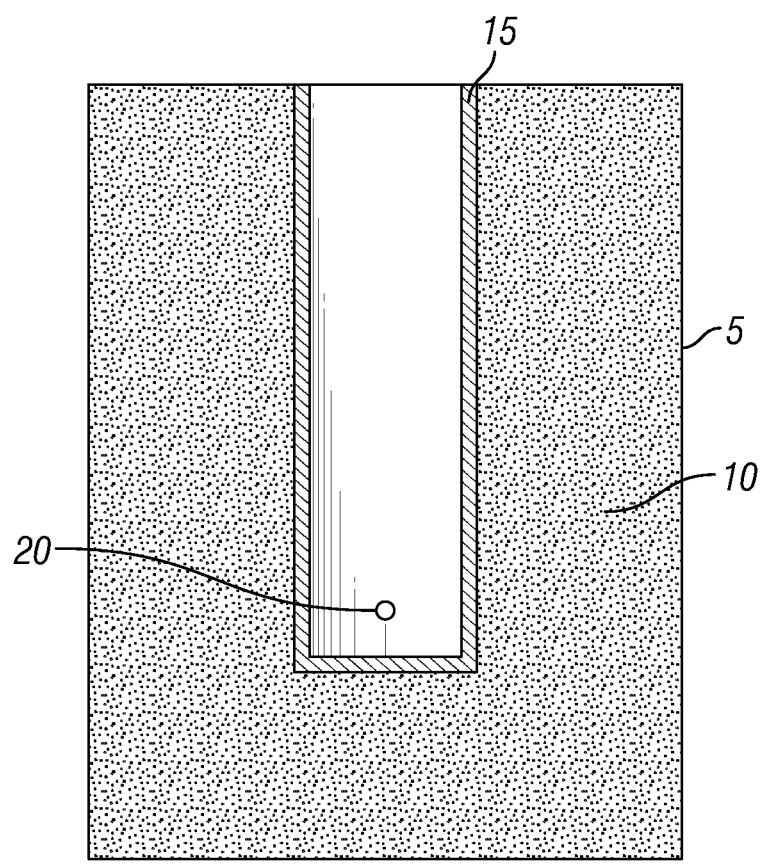
FIG. 1 illustrates an example embodiment of a method of quantifying the concentration of a radionuclide contained within a target material.

This invention relates to the field of radionuclide detection and quantification for appropriate disposal; and more specifically, to the quantification of radionuclides by measurement of single-energy gamma rays in a fixed-geometry system. In embodiments, a single-channel analyzer may be used to detect the presence of NORM and TENORM in a material (e.g., a waste material). In embodiments, a single-channel analyzer may count a gamma ray of a specific energy and in a fixed geometry such that the concentration and activity of a radionuclide may be determined. In embodiments, the activity of the radionuclide may determine the method of disposition of the material.

Embodiments comprise a single-channel analyzer. The single-channel analyzer may be any single-channel analyzer sufficient for capturing emitted gamma energy. Examples of a single-channel analyzer may include, but are not limited to scintillation-types such as sodium iodide, lanthanum bromide, cadmium-zirconium-telluride; or solid state types such high-purity germanium detectors. In some embodiments, gas-filled detectors, for example, Geiger-Mueller or ion chamber detectors may not be sufficient for quantifying the concentration of a radionuclide. More particularly, Geiger-Mueller detectors may not be viable because they do not have an energy-dependent response and as such, they cannot distinguish between high-energy and low-energy gamma emissions. Proportional counters may not be viable because their response is dependent upon detector voltage, which may change as batteries are depleted or replaced, thus significantly impacting their consistency in the field. Ionization chambers may not be viable because their detection efficiency is too low for the applications disclosed herein. The single-channel analyzer may be used to measure a specific window of gamma energy. For example, the specific window of measurable gamma energy may comprise a range encompassing 0.609 MeV. In this example, a reading of 0.609 MeV corresponds to a gamma ray emitted by Bi-214, where Bi-214 is a progeny in the decay chain of U-238. This radiation energy has an intensity of 46.1%, which refers to the percentage of disintegrations of the nuclide itself in which a gamma ray of this energy is emitted. Thus, a 0.609 MeV is emitted in the decay of Bi-214 46.1% of the time. By narrowing the specific window to a encompass a narrow range of emitted radiation energies, the single-channel analyzer may be used to quickly identify the presence of a targeted nuclide, which may in turn be used to determine the concentration and activity of the targeted radionuclide. Further, the targeted radionuclide may be used to determine the concentration of other radionuclides in the decay chain in which the targeted radionuclide is a link.

Embodiments comprise a method of quantifying the concentration of a radionuclide in a target material. A target material is any material in which it may be desirable to measure the concentration and/or activity of the radionuclides disposed within. The target material may be a waste material. The target material may be a material produced through oil and gas production, mineral processing, rare earth mineral processing, phosphate rock processing, pharmaceutical development, geothermal and/or hydrothermal energy production, or any combinations thereof. In embodiments, mineral processing may include heap-leach extraction, in situ mineral extraction, side-stream extraction of uranium, thorium processing, phosphate mining, beneficiation, wet rock handling, and/or combinations thereof. Other industries may produce the target material. In embodiments, uranium, phosphate, titanium, and/or rare earth metals from mines and/or mills may be produced as the target material. In alternate embodiments, gold mining, in situ mineral extraction, and/or the extraction and use of barite may produce the target material. Geothermal energy production may produce examples of the target material, such as scale deposits, sludges, fluids, and/or sediments. The production and consumption of coal may create the target material, in the form of fly ash. In embodiments, the inclusion of thorium dioxide during the manufacture of certain products, such as welding electrodes and/or gas lantern mantles, may produce a target material. The use of compositions such as baddeleyite in the manufacture of a product (i.e., refractory bricks) may produce the target material. Without limitation, the target material may further include drill cuttings, drilling mud, brines, development fluids, pipe scale, sludges, mine tailings, mill tailings, air and/or water filter socks, and/or combinations thereof. The target material may comprise a solid or may comprise a mixture of a solid and liquid. In embodiments, the target material may comprise nuclides and/or radionuclides. Target materials comprising radionuclides may emit radiation energy as the radionuclides decay. For example a target material comprising Ra-226 may emit gamma radiation of 0.186 MeV.

Embodiments comprise calibrating the singe-channel analyzer to detect a radionuclide of interest. For example, if the single-channel analyzer is used to detect Bi-214, the single-channel analyzer window may be set to detect the energy of a 0.609 MeV photon of emitted gamma radiation. This may be accomplished by holding the detector portion (e.g., a scintillation crystal) of the single-channel analyzer next to a radioactive source that emits the radiation energy of interest, or approximately the radiation energy of interest (e.g., the 0.609 MeV gamma ray emitted by Bi-214 as described above). The single-channel analyzer may then be adjusted to a desirable energy threshold, in embodiments, this adjustment may be performed through hardware, electronic, and/or software adjustment. For example, a threshold potentiometer may be adjusted such that the detector energy threshold is 20 keV below the radiation energy of interest. Alternatively, the detector energy threshold may be set to 30 keV below the radiation energy of interest, or further alternatively, the detector energy threshold may be set to 10 keV below the radiation energy of interest. Adjusting the detector energy threshold of the threshold potentiometer is within the capabilities of one of ordinary skill in the art and may be adjusted as desired for a specific application. Further calibration may be done by adjusting the single-channel analyzer counting window to the desired amount, for example the counting window may be adjusted to 40 keV using the window potentiometer to exclude counting any gamma rays except for those in the counting window. After adjustment, the detector of the single-channel analyzer may be held to the radioactive source again. This time, the count of emitted gamma rays above the threshold may be taken. The count rate may be recorded every 5 volts or as desired, for example every 1 volt, every 2 volts, every 3 volts, every 10 volts, and the like. The detector voltage may then be set at the level that gives the highest count rate, or alternatively that is in the middle of a plateau in the count rate. A plateau in the count rate occurs when the count rate changes very little with increasing voltage. If the count rate differs from the average value when counting a source of known strength (e.g., during a daily instrument response check) by more than 20% the meter may require recalibration or repair.

The single-channel analyzer may be used to measure the emitted radiation of any radionuclide. The radionuclide may be any decay series nuclide. For example, the radionuclide may comprise Bi-214, Ra-226, Pa-234, and the like. Factors to consider when selecting an energy window may include the intensity of the radiation energy emitted (i.e. the frequency with which gamma ray photons of a particular energy are emitted), the energy of the emitted radiation, the half-life of the isotope, whether the single-channel analyzer and consequently detector type chosen can measure the radiation energy, other radionuclides in the same decay chain, as well as other factors which would be apparent to one of ordinary skill in the art.

Embodiments comprise the measurement of background radiation at the site of the target material. Background radiation may interfere with the accuracy of the quantification of the concentration of a radionuclide. Thus, embodiments comprise measurement of the background radiation so that it may be subtracted from the gross count of radiation of the target material. In order to measure the background radiation, the single-channel analyzer may be moved away from the target material such that the majority or all of the emitted radiation energy from the target material will not be detected by the single-channel analyzer. At a sufficient distance from the target material, the single-channel analyzer may be used to count the background radiation for a specific time interval, for example, 10 minutes. The time interval may be chosen as desired and selection of a time interval to perform a background radiation count is within the purview of one of ordinary skill in the art.

In optional embodiments, a radiation safety survey may be performed. The radiation safety survey may be performed using the single-channel analyzer or any other type of analyzer, including those that may be ineffective for the methods of quantifying the concentration of a radionuclide as disclosed herein, for example, Geiger-Mueller or ion chamber detectors. The radiation safety survey may be done to ascertain a general level of radiation emitted by the target material such that appropriate safety protocols are utilized in the handling of the target material. In these optional embodiments, the analyzer may be calibrated, either as described above, or in any other appropriate manner if the analyzer is not already calibrated. Once the analyzer is calibrated, a background radiation count may be performed as disclosed above or any other sufficient manner. Once the background count has been obtained, the background count may be noted so that it may be removed, zeroed out, or otherwise subtracted from the measurement of the radiation count of the target material. For the radiation safety survey of the target material, a survey location near the target material may be selected. Once a survey location is selected, the analyzer may be used to measure the radiation count (i.e., the radiation count above background) at the survey location. This process may be repeated at multiple survey locations if desired. Appropriate safety measures, including protective clothing and isolation of the target material may be required should the target material emit an amount of radiation energy above a threshold in which one of ordinary skill in the art would deem such measures appropriate. Such threshold may be provided by environmental regulations or may otherwise be known to one of ordinary skill in the art. Further should the target material emit a level of radiation indistinguishable from the background or otherwise at a level that does not exceed a threshold set by environmental or any other type of regulation (i.e., the target material may be deemed to not comprise NORM/TENORM), then in some circumstances it may be possible to dispose of the target material without further testing.

FIG. 1 illustrates an example embodiment of a method of quantifying the concentration of a radionuclide disposed within a target material. With reference to FIG. 1, a vessel 5 is filled with target material 10. Vessel 5 may be any such vessel having a fixed geometry and capable of containing target material 10. Vessel 5 may comprise any shape having a fixed geometry. In embodiments, the vessel 5 has any shape suitable to allow the detector 20 to be placed at about the approximate center of vessel 5 and/or target material 10. In some embodiments, the vessel 5 has a cylindrical shape or a hemispherical shape. In an embodiment, vessel 5 has a cylindrical shape. Vessel 5 may be made of any material suitable for containment of a target material 10 which may comprise radionuclides. Examples of materials may include plastic, wood, metal, the like, composites thereof, or combinations thereof. Target material 10 may be obtained from any material in which a quantification of the concentration of one or more radionuclides is desired. Target material 10 may be a waste material. In embodiments, when vessel 5 is filled with target material 10, the amount of void space within vessel may be minimized, such that the vessel 5 is filled with target material 10 to as great an extent as reasonably possible. Further, in embodiments, a standard vessel 5, with a standard volume filled to a standard level and with a standard counting geometry may assist in maintaining consistency in the measurements. This may be of particular importance when averaging several sample measurements. As such, more accurate and consistent measurements may be obtained through the use a standard vessel 5 with a standard volume filled to a standard level and with a standard counting geometry. Further, should target material 10 comprise a solid mixed with a fluid, for example water, the fluid may be drained to prevent interference with the measurement. The fluid may be drained by any suitable method. Once the target material 10 is disposed within vessel 5, a protective structure 15 may be inserted into the target material 10 disposed within vessel 5. In embodiments, protective structure 15 may be inserted as close to the fixed geometric center of the target material 10 disposed within vessel 5 as reasonably possible, such that the amount of the target material 10 on any side of the protective structure 15 is approximately equal to the amount of the target material 10 on the opposing side of the protective structure 15. Additionally, the protective structure 15 may be placed such that a sufficient amount of the target material 10 surrounds all sides of the protective structure 15. In some embodiments, three inches or more of the target material 10 or more may surround all sides of the protective structure 15. In some embodiments, a range of about two inches to about four inches of target material 10 may surround all sides of the protective structure 15. In other embodiments, a range of about three inches to about four inches of target material 10 may surround all sides of the protective structure 15. In still further other embodiments, a range of about two inches to about six inches of target material 10 may surround all sides of the protective structure 15. In alternative embodiments, four inches or more of the target material 10 may surround all sides of the protective structure 15. In further alternative embodiments, five inches or more of the target material 10 may surround all sides of the protective structure 15. With the benefit if this disclosure, one of ordinary skill in the art will be able to select an amount of the target material 10 to surround the protective structure 15.

In embodiments, protective structure 15 may be made of any low density material. In some embodiments, protective structure 15 may provide the detector 20 an approximate 4π counting geometry. Protective structure 15 may protect detector 20 from contact with the target material 10 such that contamination may not occur. However protective structure 15, may not protect detector 20 from contact with any emitted radiation from the target material 10. Thus, the materials used for protective structure 15 may comprise a density low enough to allow as much emitted radiation to pass through protective structure 15 and to detector 20 as reasonably possible. Examples of protective structure 15 materials may include wood, polyvinyl chloride, aluminum, the like, combinations thereof, and/or any composites thereof. Calibration of detector 20 and a corresponding single-channel analyzer may be performed if suitable as described above. Detector 20 may be inserted into the protective structure 15 such that the detector 20 is placed as close to the fixed geometric center of the target material 10 disposed within vessel 5 as reasonably possible. Detector 20 may be coupled to a single channel analyzer. Detector 20 may comprise any type of detector 20 suitable for detecting a radiation energy emitted from a radionuclide. In an embodiment, detector 20 comprises a radiation detector comprising scintillation crystals. In embodiments, detector 20 comprises cesium iodide, sodium iodide, lanthanum bromide, cadmium-zirconium-telluride, lithium iodide, high-purity germanium, the like, or any combinations thereof.

In alternate embodiments, vessel 5 may not be used to quantify the concentration of a radionuclide disposed within target material 10. In these embodiments, target material 10 may be disposed at a certain location in a fixed state. Protective structure 15 may be inserted into target material 10 as previously discussed. Additionally, the protective structure 15 may be placed such that a sufficient amount of the target material 10 surrounds all sides of the protective structure 15. With the benefit of this disclosure, one of ordinary skill in the art will be able to select an appropriate amount of the target material 10 to surround the protective structure 15. Prior to inserting protective structure 15 into the target material 10, detector 20 may be coupled to protective structure 15. Detector 20 may be disposed within protective structure 15 so that the protective structure 15 may physically prevent the detector 20 from coming into contact with the target material 10. Detector 20 may be coupled to a single channel analyzer. The single channel analyzer may be able to take measurements directly from target material 10. In these embodiments, the target material 10 may not be prepared prior to starting the process of data collection (i.e., the protective structure 15, and the subsequent detector 20, may be inserted directly into the target material 10, without first being collected in the vessel 5). In this embodiment, the weight of the target material 10 may be approximated.

Figure 2:
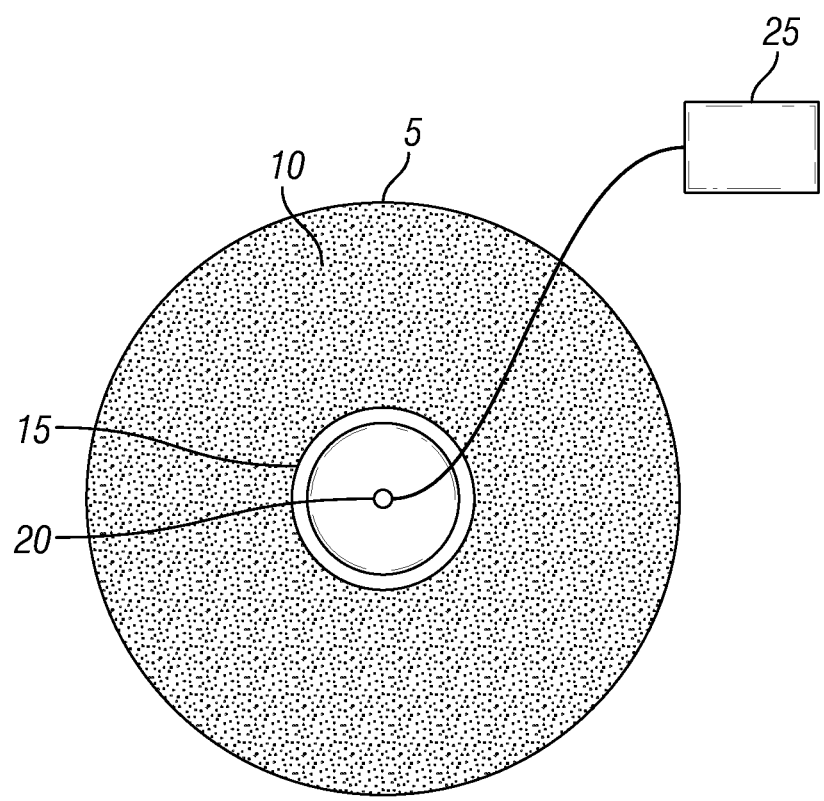
FIG. 2 illustrates another example embodiment of a method of quantifying the concentration of a radionuclide contained within a target material.

With reference to FIG. 2, single-channel analyzer 25 may be coupled to detector 20. Single-channel analyzer 25 may be used to count the emitted radiation energy from the target material 10. With detector 20 in place within protective structure 15, single-channel analyzer 25 may be used to count a window of emitted radiation energy. For example, single-channel analyzer 25 may measure an energy window set to include an emitted gamma photon of 0.609 MeV, such an emission corresponds to a decay of an atom of Bi-214. Once the window is set, the single-channel analyzer 25 may then count emitted radiation energy within the window for a time interval as desired to provide a count per time. For example, the single-channel analyzer 25 may perform a count for 1 minute, 2 minutes, 3 minutes, 4 minutes, 5 minutes, or longer as desired. With the benefit of this disclosure, one of ordinary skill in the art will be able to select a timer interval for performing a count for a specific application. After a count is performed, the counting process may be repeated on subsequent samples as desired. Once the counts are obtained, the background radiation may be subtracted from counts to produce the net count rate which may be referred to as "counts above background." Further the weight and moisture content of the target material 10 may be measured during the counting process such that the weight and moisture content of the target material 10 are reflective of the time in which the count was performed. The weight of the target material 10 is measured in order to compute a count per time per mass such as the counts per minute per mass ("CPM/M"). The moisture content may be used to correct the activity concentration of the measured radionuclide as described below. In embodiments, measuring the weight and moisture content of the target material 10 at the time in which the counts are taken may produce a more accurate measure of CPM/M as compared to measuring the weight and moisture content of the target material 10 at a later time in which the target material 10 may have drained or otherwise changed in weight and/or moisture content, such that the weight and/or moisture content of target material 10 is no longer reflective of the weight and/or moisture content of target material 10 at the time in which the counts were obtained.

Once the single-channel analyzer measurement of CPM/M is produced, the CPM/M may be converted to an activity measurement, which is a measure of radioactivity per mass. For example, if the mass of the CPM/M is in kilograms, the CPM/kg may be converted to pCi/gm. In embodiments, the conversion of the CPM/M to an activity measurement includes multiplying the CPM/M by a conversion factor. In this procedure, it is assumed that the radioactive decay series nuclides are in secular equilibrium so that they are all present in roughly equal activity concentrations. Secular equilibrium may only occur when the half-life of the unstable parent isotope is much longer than the half-life of the unstable daughter isotope. In such a case, the unstable daughter isotope emits radiation (i.e., decays to its daughter isotope) more quickly than the unstable parent isotope. Therefore, with a sufficient amount of time, the unstable daughter isotope will decay at the same rate it is produced. Thus, if all of the radionuclides in a decay chain are in secular equilibrium, the quantification of one radionuclide and consequently the activity of the same radionuclide allows for the quantification and activity of other radionuclides within the decay chain. For example, in a target material 10, such as a sample of NORM, the activity measurement of Bi-214 (or any other nuclide in the U-238 decay series) allows for the determination of the activity measurement of Ra-226. This may be of special importance in target materials 10 comprising NORM. As discussed above, NORM comprises non-man-made radionuclides; these primordial radionuclides (e.g., U-238, U-235, and Th-232) may approximately be in a state of secular equilibrium due to their age.

Unlike NORM, TENORM, although not man-made, may not be in secular equilibrium in all cases due to industrial activities which may break the secular equilibrium chain, for example, through processing to remove and/or concentrate various unstable isotopes in the decay chain. In such cases, a conversion factor that accounts for the variables noted above plus the age of the sample (i.e. the amount of time since the secular equilibrium was disturbed), may be used to determine the current state of the radionuclides present relative to the state of the radionuclides as they would be in a decay chain in secular equilibrium. The conversion factor thusly allows for correction in the sample variability. The conversion factor may be obtained by calculation and/or by comparing laboratory test results to field readings. A typical laboratory test to obtain the conversion factor may be gamma spectroscopy. Gamma spectroscopy may be used to identify the activity of all gamma emitters and thus, whether the gamma emitters are in secular equilibrium. With the benefit of this disclosure, one of ordinary skill in the art will be readily able to determine an appropriate conversion factor for a target material 10.

The laboratory analysis to obtain the conversion factor may, in some embodiments, need only be obtained once, provided the sample of target material 10 from which the conversion factor was obtained is the same as subsequent samples of target material 10 obtained from the field. For example, any subsequent samples of NORM may or may not be able to use a conversion factor obtained from a NORM sample taken from a different site, depending on the characteristics of the material being sampled and their similarity to known samples. In this case, the sample of NORM in which the conversion factor was determined may be different from the subsequent NORM samples, and therefore the conversion factor may not provide a proper conversion. As a further example, samples of TENORM that have undergone processing in which secular equilibrium is broken, may not use a conversion factor obtained from a sample of TENORM/NORM in which the processing did not occur, even if the samples were obtained from the same site. In some cases, secular equilibrium may be reestablished with time to correct these issues, as would be apparent by one of ordinary skill in the art, in which case a prior obtained conversion factor may again be used. Once the conversion factor is obtained, all field samples for which it is relevant may then be measured according to the methods disclosed herein, and may be done so without the need to send each subsequent sample to a laboratory for testing or to use complex and expensive equipment such as multi-channel analyzers. Further, the above described methods may be repeated as desired on as many samples as desired in order to obtain an average value of the activity.

After the CPM/M has been multiplied by the conversion factor to produce the activity concentration, correction of the activity concentration may be desired by applying the appropriate moisture and density correction factors as would be done by one of ordinary skill in the art. The converted and corrected activity concentration of the radionuclides present in the target material 10 may then be used to determine the disposition of the target material 10.

As discussed above, the appropriate disposition method of target material 10 may be determined based on the methods described above. The appropriate method of disposition may largely be determined by the activity concentration of specific radionuclides and any regulations regarding those specific radionuclides. For example, if an environmental or any other type of regulation restricts an activity concentration for Ra-226 to less than 5 pCi/gm, a measured average activity concentration of 4 pCi/gm for Ra-226 allows for disposal of the target material 10 without regards to the radioactivity present. Conversely, should the measured average activity concentration of Ra-226 be 7 pCi/gm, the target material 10 may be disposed of as NORM/TENORM waste according to the controlling regulations of the site in which the target material 10 is located. Disposal of NORM/TENORM typically entails disposal at a site approved for NORM/TENORM waste.

In embodiments, an information handling system may be used for the processing and display of the measurements taken from the target material 10. Without limitation in this disclosure, the information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, the information handling system may be a personal computer, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

Certain examples of the present disclosure may be implemented at least in part with non-transitory computer-readable media. For the purposes of this disclosure, non-transitory computer-readable media may include any instrumentality or aggregation of instrumentalities that may retain data and/or instructions for a period of time. Non-transitory computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

The information handling system may be coupled to the single-channel analyzer 25 through a wired and/or wireless connection. In embodiments, the information handling system may display the acquired measurements in the form of graphs, charts, images, logs, and/or the like. In alternate embodiments, the information handling system may be a mobile phone and/or tablet device. The data analysis to determine the disposition of the target material 10 may occur in a software application accessible on the mobile phone and/or tablet device. The use of the mobile phone and/or tablet device may allow for portability of the information handling system during data collection and/or data analysis. In embodiments, as the single-channel analyzer 25 is taking measurements, those measurements may be remotely uploaded to the mobile phone and/or tablet device. In alternate embodiments, the mobile phone and/or tablet device may be coupled to the single-channel analyzer 25 during data collection, and the mobile phone and/or tablet device may be decoupled from the single-channel analyzer 25 for data analysis while the mobile phone and/or tablet device is in transit. The mobile phone and/or tablet device may have a wired and/or wireless connection with the single-channel analyzer 25.

Although the present invention and its advantages have been described in detail, it should be understood that various changes, substitutions and alterations may be made herein without departing from the spirit and scope of the invention as defined by the appended claims.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the invention. If there is any conflict in the usages of a word or term in this specification and one or more patent(s) or other documents that may be incorporated herein by reference, the definitions that are consistent with this specification should be adopted.

What is claimed is:

1. A method for determining a radionuclide concentration of a material comprising:
    placing a detector within the material, wherein the detector is coupled to a single-channel analyzer;
    wherein the material comprises a radionuclide;
    measuring the moisture content of the material to be analyzed;
    counting the emitted radiation having a known energy over an interval of time to produce a count per time, wherein the emitted radiation is emitted from the radionuclide; and
    dividing the count per time by the weight of the material to produce a count per time per weight.

2. The method of claim 1, further comprising approximating the weight of the material to be analyzed.

3. The method of claim 1, further comprising displaying the count per time per weight in the form of graphs, charts, images, logs, or any combinations thereof.

4. The method of claim 3, wherein displaying the acquired measurements occurs on an information handling system, wherein the information handling system is a mobile phone.

5. The method of claim 1, wherein the material comprises drill cuttings, drilling mud, brines, development fluids, pipe scale, sludges, mine tailings, mill tailings, air filter socks, water filter socks, or any combinations thereof.

6. The method of claim 1, wherein the material is a by-product of oil and gas production, mineral processing, phosphate rock processing, pharmaceutical development, geothermal energy production, hydrothermal energy production, or combinations thereof.

7. The method of claim 1, further comprising multiplying the count per time per weight by a conversion factor to produce an activity concentration.

8. The method of claim 7, further comprising correcting the activity concentration by applying a moisture correction factor.

9. The method of claim 1, wherein the emitted radiation comprises gamma radiation, wherein the radionuclide is Ra-226, or Pa-234.

10. The method of claim 1, further comprising correcting the activity concentration by applying a density correction factor.

11. The method of claim 1, wherein the method is repeated to obtain multiple counts per time per weight, wherein the multiple counts per time per weight are averaged to produce an average count per time per weight.

12. A system for characterizing the radionuclide content of a material comprising:
    a vessel for containing a material, wherein the material comprises a radionuclide;
    a detector inserted into the vessel, wherein the detector is coupled to a single-channel analyzer; and
    an information handling system, wherein the information handling system processes measurements acquired by the single-channel analyzer.

13. The system of claim 12, wherein the information handling system is a mobile phone, wherein the mobile phone is wirelessly connected to the single-channel analyzer.

14. The system of claim 13, wherein the mobile phone comprises a software application.

15. The system of claim 12, wherein the information handling system is a tablet device, wherein the tablet device is connected by wire to the single-channel analyzer.

16. The system of claim 15, wherein the tablet device comprises a software application.

17. The system of claim 12, wherein the material comprises drill cuttings, drilling mud, brines, development fluids, pipe scale, sludges, mine tailings, mill tailings, air filter socks, water filter socks, or any combinations thereof.

18. The system of claim 12, wherein the material is a by-product of oil and gas production, mineral processing, phosphate rock processing, pharmaceutical development, geothermal energy production, hydrothermal energy production, or combinations thereof.

19. The system of claim 12, wherein the radionuclide is Ra-226, or Pa-234.

20. The system of claim 12, wherein the information handling system is configured to:
   measure the moisture content of the material;
   approximate the weight of the material;
   count the emitted radiation having a known energy over an interval of time to produce a count per time;
   divide the count per time by the weight of the material to produce a count per time per weight;
   multiply the count per time per weight by a conversion factor to produce an activity concentration;
   correct the activity concentration by applying a moisture correction factor and a density correction factor; and
   obtain multiple counts per time per weight, wherein the multiple counts per time per weight are averaged to produce an average count per time per weight.

\* \* \* \* \*